United States Patent
Stoll et al.

(10) Patent No.: US 10,808,240 B2
(45) Date of Patent: Oct. 20, 2020

(54) AUTOMATED AND MANUAL METHODS FOR ISOLATION OF EXTRACELLULAR VESICLES AND CO-ISOLATION OF CELL-FREE DNA FROM BIOFLUIDS

(71) Applicant: Exosome Diagnostics, Inc., Waltham, MA (US)

(72) Inventors: Georg Stoll, Waltham, MA (US); Daniel Enderle, Waltham, MA (US); Mikkel Noerholm, Martinsried (DE); Johan Karl Olov Skog, Charlestown, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 0 days.

(21) Appl. No.: 16/301,176

(22) PCT Filed: May 15, 2017

(86) PCT No.: PCT/US2017/032719
§ 371 (c)(1),
(2) Date: Nov. 13, 2018

(87) PCT Pub. No.: WO2017/197399
PCT Pub. Date: Nov. 16, 2017

(65) Prior Publication Data
US 2019/0284548 A1    Sep. 19, 2019

Related U.S. Application Data

(60) Provisional application No. 62/336,203, filed on May 13, 2016.

(51) Int. Cl.
| C12N 15/10 | (2006.01) |
| C12N 15/11 | (2006.01) |
| C07H 1/06  | (2006.01) |

(52) U.S. Cl.
CPC .......... *C12N 15/1006* (2013.01); *C12N 15/11* (2013.01); *C07H 1/06* (2013.01)

(58) Field of Classification Search
CPC ..... C12N 15/1006; C12N 15/11; C07H 1/056
See application file for complete search history.

(56) References Cited

U.S. PATENT DOCUMENTS

| 5,219,727 A | 6/1993 | Wang et al. |
| 5,538,871 A | 7/1996 | Nuovo et al. |
| 5,556,773 A | 9/1996 | Yourno |
| 5,639,606 A | 6/1997 | Willey |
| 5,639,611 A | 6/1997 | Wallace et al. |
| 6,004,755 A | 12/1999 | Wang |
| 6,812,023 B1 | 11/2004 | Lamparski et al. |
| 6,893,837 B2 | 5/2005 | Slamon et al. |
| 6,899,863 B1 | 5/2005 | Dhellin et al. |
| 6,913,879 B1 | 7/2005 | Schena |
| 6,994,960 B1 | 2/2006 | Foote et al. |
| 7,074,563 B2 | 7/2006 | Köster |
| 7,186,512 B2 | 3/2007 | Martienssen et al. |
| 7,198,893 B1 | 4/2007 | Köster et al. |
| 7,198,923 B1 | 4/2007 | Abrignani et al. |
| 7,364,848 B2 | 4/2008 | Van Beuningen et al. |
| 7,378,245 B2 | 5/2008 | Liu |
| 10,465,183 B2 * | 11/2019 | Skog ................. C12N 15/1006 |

FOREIGN PATENT DOCUMENTS

| WO | WO 2003/023065 A1 | 3/2003 |
| WO | WO 2006/113590 A2 | 10/2006 |
| WO | WO 2009/100029 A1 | 8/2009 |
| WO | WO 2014/107571 A1 | 7/2014 |
| WO | WO 2015/120445 A1 | 8/2015 |
| WO | WO 2016/007755 A1 | 1/2016 |
| WO | WO 2017/197399 A1 | 11/2017 |

OTHER PUBLICATIONS

Abravaya, et al., "Detection of point mutations with a modified ligase chain reaction (Gap-LCR)." Nucleic Acids Research (1995); 23(4): 675-682.

Al-Nedawi, et al., "Intercellular transfer of the oncogenic receptor EGFRvIII by microvesicles derived from tumour cells." Nat Cell Biol. (2008); 10(5): 619-624.

Appliedbiosystems, "MagMAX Cell-Free DNA Isolation Kit—Isolation of cfDNA from urine samples." Thermo Fisher Scientific (2016); Pub. No. MAN0015628, Retrieved on Feb. 5, 2019, 3 pages.

Balzar, et al., "The biology of the 17-1A antigen (Ep-CAM)." J Mol Med. (1999); 77(10): 699-712.

Bettegowda, et al., "Detection of Circulating Tumor DNA in Early- and Late-Stage Human Malignancies." Science Translational Medicine (Feb. 2014); 6(224): 224ra24.

Chen, et al., "Microfluidic isolation and transcriptome analysis of serum microvesicles." Lab Chip (2010); 10(4): 505-511.

Cheruvanky, et al., "Rapid isolation of urinary exosomal biomarkers using a nanomembrane ultrafiltration concentrator." Am J Physiol Renal Physiol. (2007); 292: F1657-F1661.

Cotton, et al., "Reactivity of cytosine and thymine in single-base-pair mismatches with hydroxylamine and osmium tetroxide and its application to the study of mutations." Proc Natl Acad Sci U S A (1988); 85 (12): 4397-4401.

(Continued)

*Primary Examiner* — Lawrence E Crane
(74) *Attorney, Agent, or Firm* — Cooley LLP; Ivor R. Elrifi; Matthew Pavao

(57) ABSTRACT

The invention provides novel methods and kits for fully automated high-throughput method for isolation of extracellular vesicles and co-isolation of cell-free DNA from biofluids, including cell-free DNA and/or cell-free DNA and nucleic acids including at least RNA from microvesicles, novel methods and kits for isolation of extracellular vesicles and co-isolation of cell-free DNA from biofluids, including cell-free DNA and/or cell-free DNA and nucleic acids including at least RNA from microvesicles that do not require the use of phenol or chloroform, and for extracting nucleic acids from the extracellular vesicles and/or from the biological samples.

14 Claims, 1 Drawing Sheet

(56) References Cited

OTHER PUBLICATIONS

Enderle et al., "Characterization of RNA from Exosomes and other Extracellular Vesicles Isolated by a Novel Spin Column-Based Method", PLoS One (2015); 10(8): e0136133, pp. 1-19.

Enderle et al., "Development of a one-step isolation platform for exosomal RNA and circulating cell-free DNA from cancer plasma samples", European Journal of Cancer, (2014); 50 (6): p. 102.

Fischer and Lerman, "[11] Two-dimensional electrophoretic separation of restriction enzyme fragments of DNA." Methods in Enzymology (1979); 68: 183-191.

Fischer and Lerman, "Length-independent separation of DNA restriction fragments in two-dimensional gel electrophoresis." Cell (1979); 16(1): 191-200.

Guatelli, et al., "Isothermal, in vitro amplification of nucleic acids by a multienzyme reaction modeled after retroviral replication." Proc Natl Acad Sci U S A (1990); 87: 1874-1878.

Hahn, "Molecular biology of double-minute chromosomes." BioEssays (1993); 15(7): 477-484.

International Preliminary Report on Patentability for International Application No. PCTUS2017032719, dated Nov. 13, 2018, 11 pages.

International Search Report and Written Opinion for International Application No. PCTUS2017032719, dated Nov. 16, 2017, 17 pages.

Invitation to Pay Additional Fees for International Application No. PCTUS2017032719, mailed Jul. 31, 2017, 15 pages.

Kan and Dozy, "Antenatal diagnosis of sickle-cell anaemia by DNA analysis of amniotic-fluid cells." The Lancet (1978); 312(8096): 910-912.

Kan and Dozy, "Polymorphism of DNA sequence adjacent to human β-globin structural gene: relationship to sickle mutation." PNAS (1978); 75(11): 5631-5635.

Kirsch, et al., "An Improved Method for the Isolation of Free-Circulating Plasma DNA and Cell-Free DNA from Other Body Fluids." Annals of the New York Academy of Sciences (2012); 1137 (1): 135-139.

Kwoh, et al., "Transcription-based amplification system and detection of amplified human immunodeficiency virus type 1 with a bead-based sandwich hybridization format." Proc Natl Acad Sci U S A (1989); 86: 1173-1177.

Landegren, et al., "A ligase-mediated gene detection technique." Science (1988); 241(4869): 1077-1080.

Li, et al., "BEAMing up for detection and quantification of rare sequence variants." Nat Methods. (2006); 3(2): 95-97.

Li, et al., "Replacing PCR with COLD-PCR enriches variant DNA sequences and redefines the sensitivity of genetic testing." Nature Medicine (2008); 14(5): 579-584.

Miele, et al., "Autocatalytic replication of a recombinant RNA." J Mol Biol. (1983); 171: 281-295.

Miranda, et al., "Nucleic acids within urinary exosomes/microvesicles are potential biomarkers for renal disease." Kidney International (2010); 78(2): 191-199.

Myers, et al., "Detection of single base substitutions by ribonuclease cleavage at mismatches in RNA:DNA duplexes." Science (1985); 230(4731): 1242-1246.

Nakazawa, et al., "UV and skin cancer: specific p53 gene mutation in normal skin as a biologically relevant exposure measurement." Proc Natl Acad Sci U S A. (1994); 91: 360-364.

Nilsson, et al., "Prostate cancer-derived urine exosomes: a novel approach to biomarkers for prostate cancer." British Journal of Cancer (2009); 100: 1603-1607.

Noerholm, et al., "RNA expression patterns in serum microvesicles from patients with glioblastoma multiforme and controls." BMC Cancer (2012); 12 (1): 11 pages.

Orita, et al., "Detection of polymorphisms of human DNA by gel electrophoresis as single-strand conformation polymorphisms." PNAS (1989); 86(8): 2766-2770.

Raposo, et al., "B lymphocytes secrete antigen-presenting vesicles." Journal of Experimental Medicine (1996); 183: 1161-1172.

Skog, et al., "Glioblastoma microvesicles transport RNA and proteins that promote tumour growth and provide diagnostic biomarkers." Nature Cell Biology (2008); 10(12): 1470-1476.

Steemers, et al., "Whole-genome genotyping with the single-base extension assay." Nature Methods (2006); 3: 31-33.

Taylor and Gercel-Taylor, "MicroRNA signatures of tumor-derived exosomes as diagnostic biomarkers of ovarian cancer." Gynecol Oncol. (2008); 110: 13-21.

Tzimagiorgis, et al., "Recovering circulating extracellular or cell-free RNA from bodily fluids." Cancer Epidemiology (2011); 35 (6): 580-589.

Velculescu, et al., "Serial Analysis of Gene Expression." Science (1995); 270(5235): 484-487.

Went et al., "Frequent epcam protein expression in human carcinomas." Hum Pathol. (2004); 35:122-128.

\* cited by examiner

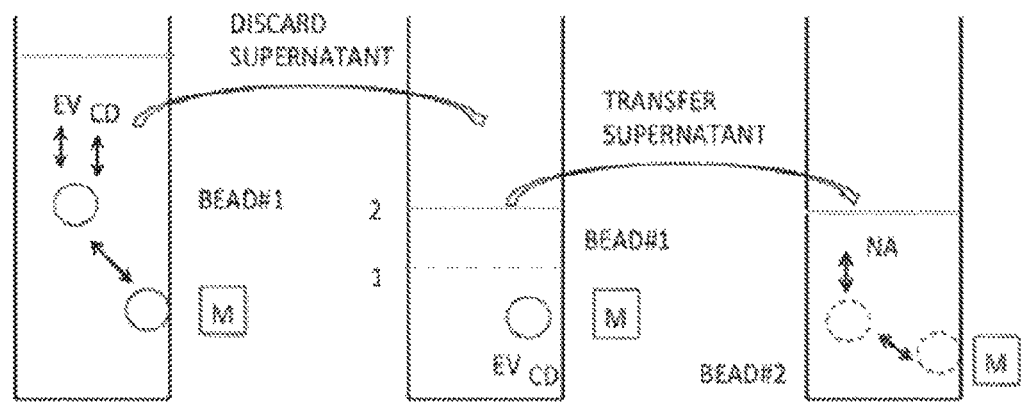

AUTOMATED AND MANUAL METHODS FOR ISOLATION OF EXTRACELLULAR VESICLES AND CO-ISOLATION OF CELL-FREE DNA FROM BIOFLUIDS

RELATED APPLICATIONS

This application is a U.S. National Stage Application, filed under 35 U.S.C. 371, of International Application No. PCT/US2017/032719, filed on May 15, 2017, which claims priority to, and the benefit of, U.S. Provisional Application No. 62/336,203, filed May 13, 2016, the contents of each of which are incorporated herein by reference in their entirety.

FIELD OF THE INVENTION

The invention provides novel methods and kits for fully automated high-throughput method for isolation of extracellular vesicles and co-isolation of cell-free DNA from biofluids, including cell-free DNA and/or cell-free DNA and nucleic acids including at least RNA from microvesicles, novel methods and kits for isolation of extracellular vesicles and co-isolation of cell-free DNA from biofluids, including cell-free DNA and/or cell-free DNA and nucleic acids including at least RNA from microvesicles that do not require the use of phenol or chloroform, and for extracting nucleic acids from the extracellular vesicles and/or from the biological samples.

BACKGROUND

In molecular biology, the preparation of pure, isolated molecules from mixed organic materials such as plants, microbial cultures, animal tissue and blood, is of central importance. It is the prerequisite for many downstream processes that analyze the isolated material. Various approaches to sample isolation technology exist and not all are equally well suited for every application. Especially, when the molecules in the sample material are limited and the downstream assay technology aims to be highly sensitive, extraction technology is paramount. This is the case for liquid biopsies, where human biofluids are analyzed with diagnostic purpose in mind. Here, technological advance in sample isolation can have a broad and profound impact on the current standard of care.

Human biofluids contain cells and also cell-free sources of molecules. Cell-free sources include extracellular vesicles and the molecules carried within (e.g. RNA, DNA, lipids, small metabolites and proteins) and also cell-free DNA, which is likely to be derived from apoptotic and necrotic tissue. Because the absolute amount of molecules from each source is low (e.g. Bettegowda et al. 2014 Sci Transl Med), it is desirable to co-isolate all available molecules from a clinical sample volume and to be able to use a high amount of starting material. Furthermore, it is desirable to automate the extraction method on liquid handling devices for low-cost/high throughput extraction.

Accordingly, there is a need for bead-based methods for the co-extraction of extracellular vesicles and cell-free DNA from the same volume of a biofluids, and methods of extracting high quality nucleic acids for accurate diagnosis of medical conditions and diseases.

SUMMARY OF THE INVENTION

The present invention provides novel methods and kits for improved methods for the isolation of isolation of extracellular vesicles and co-isolation of cell-free DNA from biofluids, including cell-free DNA and/or cell-free DNA and nucleic acids including at least RNA from microvesicles. In one aspect, these novel methods and kits provide for automated isolation of extracellular vesicles and co-isolation of cell-free DNA from biofluids, including cell-free DNA and/or cell-free DNA and nucleic acids including at least RNA from microvesicles. In another aspect, these novel methods and kits provide for isolation of extracellular vesicles and co-isolation of cell-free DNA from biofluids, including cell-free DNA and/or cell-free DNA and nucleic acids including at least RNA from microvesicles that do not require the use of phenol or chloroform.

The disclosure provides methods for extracting DNA and RNA from a biological sample comprising: (a) providing a biological sample; (b) contacting the biological sample with a solid capture surface under conditions sufficient to retain cell-free DNA and microvesicles from the biological sample on or in the capture surface, and (c) contacting the capture surface with a GTC-based elution buffer while cell-free DNA and the microvesicles are on or in the capture surface, thereby releasing the DNA and RNA from the sample and producing a homogenate.

The disclosure also provides methods for extracting DNA and RNA from a biological sample comprising: (a) providing a biological sample; (b) contacting the biological sample with a solid capture surface under conditions sufficient to retain cell-free DNA and microvesicles from the biological sample on or in the capture surface, and (c) contacting the capture surface with a GTC-based elution buffer while cell-free DNA and the microvesicles are on or in the capture surface, thereby releasing the DNA and RNA from the sample and producing a homogenate; and (d) extracting the DNA, the RNA, or both the DNA and RNA from the homogenate.

In some embodiments, the solid capture surface is a bead. In some embodiments, the solid capture surface is a membrane. In some embodiments, the solid capture surface is magnetic. In some embodiments, the bead is an ion exchange (IEX) bead. In some embodiments, the bead is positively charged. In some embodiments, the bead is negatively charged. In some embodiments, the bead is functionalized with quaternary amines. In some embodiments, the bead is functionalized with sulfate, sulfonate, tertiary amine, any other IEX group, and any combination thereof. In some embodiments, the IEX bead is a magnetic, high capacity IEX bead. In some embodiments, the IEX bead is a strong ferromagnetic, high capacity bead. In some embodiments, the IEX bead is a strong ferromagnetic, high capacity, iron oxide-containing magnetic polymer. In some embodiments, the IEX bead has no surface exposed to the liquid that is prone to oxidization. In some embodiments, the IEX bead has a high ratio of bead charge to exposed surface.

In some embodiments, the biological sample is plasma, serum or urine. In some embodiments, the volume of the biological sample is from 0.2 to 20 mL.

In some embodiments, the biological sample is a urine sample, wherein the urine sample is collected using a first-catch urine collection device. In some embodiments, the first-catch urine collection device is EZPZ, Colli-Pee or other commercially available first-catch collection devices.

In some embodiments, the GTC-based elution buffer comprises a denaturing agent, a detergent, a buffer substance, and combinations thereof. In some embodiments, the GTC-based elution buffer comprises a denaturing agent and a reducing agent. In some embodiments, the reducing agent is β-Mercaptoethanol (BME). In some embodiments, the reducing agent is tris(2-carboxyethyl)phosphine (TCEP). In some embodiments, the reducing agent is DTT.

In some embodiments, step (d) further comprises adding protein precipitation buffer to the homogenate prior to extraction of the DNA, the RNA, or both the DNA and RNA from the homogenate.

In some embodiments, step (d) further comprises an enzymatic digestion. In some embodiments, the step (d) comprises a proteinase digestion. In some embodiments, the step is performed with or without previous elution of material from the solid surface. In some embodiments, the step is performed with an optimal temperature, GTC concentration, detergent content, enzyme concentration and time.

In some embodiments, step (d) comprises a digestion using proteinase, DNAse, RNase, or a combination thereof. In some embodiments, the protein precipitation buffer comprises a transition metal ion, a buffering agent, or both a transition metal ion and a buffering agent. In some embodiments, the transition metal ion is zinc. In some embodiments, one or more subsequent buffers contains at least one substance to counteract the potential carryover of the transition ion into the downstream assay. In some embodiments, the counteracting substance is a chelating agent. In some embodiments, the counteracting substance EDTA. In some embodiments, at least one additional chelator of bivalent cations is used.

In some embodiments, the protein precipitation buffer has defined pH range from 3.1 to 4.1. In some embodiments, the buffering agent is sodium acetate (NaAc).

In some embodiments, step (a) further comprises processing the biological sample by filtering the biological sample. In some embodiments, the filtration is performed using a 0.8 µm filter.

In some embodiments, step (b) further comprises a centrifugation step after contacting the biological sample with the capture surface.

In some embodiments, step (b) further comprises washing the capture surface after contacting the biological sample with the capture surface.

In some embodiments, step (c) further comprises a centrifugation step after contacting the capture surface with the GTC-based elution buffer.

In some embodiments, step (d) further comprises adding a nucleic acid control spike-in to the homogenate.

In some embodiments, the method further comprises step (f) binding of protein precipitated-eluate to a silica column; and (h) eluting the extraction from the silica column.

In some embodiments, step (c) comprises an elution of intact vesicles from the surface. In some embodiments, the method uses a change in pH. In some embodiments, the method uses a change in ionic strength.

In any of the embodiments provided herein, the methods can be adapted for use in any high throughput methods for isolation of extracellular vesicles and/or cell-free DNA. In some embodiments, all steps use magnetic beads as a solid capture surface. In some embodiments, the method is implemented on a robotic liquid handling platform. In some embodiments, the method is implemented on a microfluidic point-of-care device. In some embodiments, an orbital shaker or other mixing device is used to effectively bind the isolate to the surface.

In some embodiments, step (d) comprises using silica-based solid surface. In some embodiments, the solid surface is a spin-column membrane. In some embodiments, the solid surface is a bead.

In some embodiments, step (b) comprises using a chemical crowding agent to enhance binding of EVs and cfDNA to the beads. In some embodiments, substance that functions as a chemical crowding agent is polyethylene glycol (PEG). In some embodiments, the substance is polyethylene glycol in a concentration range of 0.5-10% w/v).

In some embodiments, step (d) comprises using one or multiple chemicals to enhance the binding of small RNAs to the solid surface. In some embodiments, the substances consist of optimal concentration of isopropanol, sodium acetate and glycogen. In some embodiments, the small RNAs are micro RNAs (miRNA)

In some embodiments, step (d) comprises using the same beads used for part (c). In some embodiments, the beads are directly used in a downstream assay.

In some embodiments, step (d) is omitted. In some embodiments, the solid surface is directly used in a downstream assay. In some embodiments, the downstream assay is a reverse transcription followed by a quantitative polymerase chain reaction (RT-qPCR).

In some embodiments, the leftover liquid volume is used to analyze non-bound plasma components. In some embodiments, the components are Ago2 protein-bound miRNAs.

In some embodiments, step (d) is further modified to isolate the protein component of the homogenate.

In some embodiments, step (d) does not make use of an extraction with an organic solvent.

In some embodiments, two consecutive isolation principles are used to enhance the purity of the isolated molecular analytes. In some embodiments, the two isolation principles are solid surfaces of ion exchange and silica purification.

In some embodiments, step (b) utilizes different populations of solid capture surfaces. In some embodiments, the solid capture surfaces are exposed to the sample volume sequentially. In some embodiments, the solid capture surfaces are exposed to the sample volume in a single step.

In some embodiments, step (b) utilizes an optimal combination of binding conditions that may encompass concentration of cations, concentration of anions, detergents, pH, time and temperature, and any combination thereof. In some embodiments, the optimal concentration of sodium chloride is in the range of 50-500 mM.

The disclosure also provides methods for extracting DNA and RNA from a biological sample comprising: (a) providing a urine sample, wherein the urine sample is collected using a first-catch urine collection device; (b) contacting the urine sample with a solid capture surface under conditions sufficient to retain cell-free DNA and microvesicles from the biological sample on or in the capture surface; and (c) contacting the capture surface with a GTC-based elution buffer while cell-free DNA and the microvesicles are on or in the capture surface, thereby releasing the DNA and RNA from the urine sample and producing a homogenate. In some embodiments, the method further comprises step (d) extracting the DNA, the RNA, or both the DNA and RNA from the homogenate. In some embodiments, the homogenate is used in a downstream assay. In some embodiments, the solid surface is directly used in a downstream assay. In some embodiments, the downstream assay is a reverse transcription followed by a quantitative polymerase chain reaction (RT-qPCR). In some embodiments, the first-catch urine collection device is EZPZ, Colli-Pee or other commercially available first-catch collection devices.

The disclosure also provides methods for isolating exosomes and extracellular vesicles (EVs) in a biofluid sample, the method comprising providing a charged capture surface, contacting the biofluid sample and the charged capture surface in the presence of a chemical crowding agent to enhance binding of exosomes and EVs to the charged capture surface.

This method can be used in conjunction with any of the capture surfaces, buffers, other reagents, and/or conditions described herein. In some embodiments, the chemical crowding agent is polyethylene glycol (PEG). In some embodiments, the solid capture surface is a bead. In some embodiments, the solid capture surface is a column membrane. In some embodiments, the solid capture surface is magnetic. In some embodiments, the bead is an ion exchange (IEX) bead. In some embodiments, the bead is positively charged. In some embodiments, the bead is negatively charged. In some embodiments, the bead is functionalized with quaternary amines. In some embodiments, the bead is functionalized with sulfate, sulfonate, tertiary amine, any other IEX group, and any combination thereof. In some embodiments, the IEX bead is a magnetic, high capacity IEX bead. In some embodiments, the IEX bead is a strong ferromagnetic, high capacity bead. In some embodiments, the IEX bead is a strong ferromagnetic, high capacity, iron oxide-containing magnetic polymer. In some embodiments, the IEX bead has no surface exposed to the liquid that is prone to oxidization. In some embodiments, the IEX bead has a high ratio of bead charge to exposed surface. In some embodiments, the biological sample is plasma, serum, or urine. In some embodiments, the biological sample is between 0.2 to 20 mL. In some embodiments, wherein the biological sample is urine, and wherein the urine sample is collected using a first-catch urine collection device.

The present invention is a method for bead-based extraction of extracellular vesicles and co-extraction of cell-free DNA from biofluids. The methods provided herein are useful, as an automatable version of an isolation technology allows for high-throughput applications for routine use, e.g. in clinical laboratories processing many samples. The methods provided herein use charge-based ion exchange chromatography(IEX) to isolate the extracellular vesicles and/or cell-free DNA. Those of ordinary skill in the art will appreciate that methods of using charged based IEX for vesicle isolation are not straightforward and that not all beads are strong enough IEX beads to successfully, reliably, and efficiently isolate extracellular vesicles and/or cell free DNA.

For cell-free DNA (cf-DNA), several methods exist that allow extraction from biofluids mostly based on whole-volume biofluid lysis and subsequent DNA extraction using silica membrane columns or silica beads. For extraction of extracellular vesicles (EVs) from biofluids, previous methodology entails either columns or precipitation based methods or bead-based methods that rely on antibodies to isolate only a sub-population of vesicles. However, there is no current method of bead-based co-extraction of extracellular vesicles and cell-free DNA from the same volume of a biofluid.

The methods of the disclosure provide a reaction designed to capture and concentrate EVs and co-capture cell-free DNA from large volumes of biofluids using magnetic beads. Also, the methods of the disclosure provide reactions downstream of the capture to release and purify the molecular content of the isolate, also based on magnetic beads. The methods of the disclosure have been designed to be easily adapted on liquid handling machines.

In one embodiment, all DNA and RNA from the isolate is extracted. In some embodiments, the methods includes a first step in which high-capacity ion exchange (IEX) magnetic beads are used for a single-step isolation of EVs and co-isolation of cell-free DNA from the same volume of biofluid. For a bead-based isolation of EVs by IEX, a high capacity IEX matrix is required. For a bead-based isolation of cell-free DNA only, a lower capacity would suffice. Large amounts of lower capacity magnetic beads, are impractical for handling and need extensive separation times. The methods provided herein utilize a new type of magnetic bead which has a high IEX capacity by design and also allows using higher bead volumes without the handling issues seen with other beads.

Magnetic high-capacity IEX beads capture both EVs and cfDNA. Magnetic high-capacity IEX beads capture all EVs, not only EV subpopulations. In some embodiments, if needed, intact vesicles can be eluted from the IEX beads by high salt conditions.

In some embodiments, vesicle-depleted and cfDNA-depleted supernatant can be used e.g. for creating complementary data points (e.g. free protein content, protein-bound miRNAs, etc.).

Chemical formulation of the binding and wash buffers, incubation time, bead amount, and temperature are parameters in isolation success.

Differential binding of EVs and cfDNA can be achieved by altering said parameters.

Large (IEX) beads allow for the use of strong ferromagnetic material, enabling fast separation times and more flexible use of many magnetic devices and plastic-ware.

In some embodiments, the methods include a second step in which the material bound to the magnetic high-capacity IEX beads is lysed in a first reaction and conditioned for binding to NA-isolation beads in a second reaction. Lysis is performed using a concentrated, strong denaturing agent. Conditioning consists of lysate dilution and proteinase digestion. Proteinase digestion is used here as an easily automatable step (as opposed to Phenol-Chloroform extraction or protein precipitation).

In some embodiments, the methods include a third step in which the lysed nucleic acids are co-bound, washed and eluted to the magnetic silica beads.

Beads bind miRNAs, mRNA and DNA. Beads are able to be eluted with small volumes of elution buffer.

In one embodiment, these methods may be used to extract nucleic acids from biofluids. In another embodiment, these methods may be used to isolate intact vesicles and circulating nucleosomes. In another embodiment, the methods may be used to isolate proteins, lipids or other molecules.

In some embodiments, the method includes the use of solid capture matrix. In some embodiments, solid matrix is a population of solid beads, a population of porous-emulsion derived beads, one or more gel, a polymer slurry, any other suitable solid matrix, or combinations thereof.

In some embodiments, the solid capture matrix is used to capture an entity such as, for example, exosomes, cell-free DNA, or co-isolation of cfDNA+exosomes.

In some embodiments, the solid capture matrix is magnetic, and the captured entity is isolated by magnetism. In some embodiments, the solid capture matrix is non-magnetic, and the captured entity is isolated by gravitational force, centrifugation or filtration.

In some embodiments, the solid capture matrix is surface-modified. In some embodiments, the surface of the solid capture matrix is modified with the following: TEX, antibodies, receptors-ligands, and/or combinations thereof.

In some embodiments, the captured entities are released from the solid capture matrix either by: non-denaturing, non-lysing high salt conditions for isolation of intact vesicles, by lysing conditions for downstream isolation of nucleic acids, DNA, RNA, proteins, and/or nucleic acids+ proteins.

In some embodiments, the lysis conditions are achieved by non-phenol based lysis, by tri-reagent based lysis, or by combinations thereof.

In some embodiments, the nucleic acid isolation from the lysed solution is performed by: magnetic silica beads, non-magnetic silica beads, silica column, or combinations thereof.

In some embodiments, the methods include the step of protein removal from lysed solution to improve nucleic acid recovery from silica adhesion. In some embodiments, protein removal is accomplished by: proteinase digestion, phenol-chloroform extraction, protein precipitation, or combination thereof.

In some embodiments, the methods do not include the step of protein removal.

In some embodiments, the methods include the step of protein precipitation with $ZnCl_2$. In some embodiments, the protein precipitation is accomplished by surplus cation removal by complex binding (e.g., by EDTA).

The present invention provides methods for isolation of cell-free DNA ("cfDNA," also known as circulating DNA) and/or for the combined isolation of cfDNA and nucleic acids including at least the RNA from microvesicles from a sample by capturing the DNA and/or DNA and RNA to a surface, subsequently lysing the microvesicles to release the nucleic acids, particularly RNA, contained therein, and eluting the DNA and/or DNA and nucleic acids including at least RNA from the capture surface. Those of ordinary skill in the art will appreciate that the microvesicle fraction also includes DNA. Thus, lysis of the microvesicle fraction releases both RNA and DNA.

RNA from the microvesicle fraction is thought to be derived from living cells in e.g. a diseased tissue. Cell-free (cf) DNA is thought to be derived from dying cells, e.g. necrotic cells in a disease tissue. Thus, detection of the cfDNA can be useful as an indicator of therapy response, while detection of the RNA from microvesicles can be useful as an indicator of resistance mutations on the rise. The methods provided herein combine both sources of nucleic acid and are, therefore useful in allowing for the analysis of both mechanisms.

The methods provided herein are suitable for any of a variety of clinical indications. Previous procedures used to isolate and extract nucleic acids from a sample, e.g., cfDNA and/or DNA and nucleic acids including at least RNA from the microvesicle fraction of a sample, relied on the use of hazardous substances such as, for example, a distinct phenol/chloroform purification step during nucleic acid extraction. The methods and kits for isolation and extraction provided herein overcome these disadvantages and provide a spin-based column for isolation and extraction that is fast, robust, easily scalable to large volumes, and does not include the use of hazardous substances.

Furthermore, the methods provided herein also allow for the isolation and extraction of other, non-nucleic acid biomarkers, such as, for example, proteins from the microvesicle fraction, in a variety of biological samples. Like the isolated nucleic acids, these additional biomarkers such as proteins from microvesicles can then be further analyzed using any of a variety of art-recognized assays and other techniques such as qPCR and next-generation sequencing (NGS) assays. These protein and/or nucleic acid biomarkers are also useful in any of a variety of diagnostic applications.

The methods and kits isolate and extract nucleic acids, e.g., DNA and/or DNA and nucleic acids including at least RNA from a sample. In some embodiments, the methods and kits using the following general procedure. First, the nucleic acids in the sample, e.g., the DNA and/or the DNA and the microvesicle fraction, are bound to a capture surface such as a membrane filter, and the capture surface is washed. Then, an elution reagent is used to perform on-membrane lysis and release of the nucleic acids, e.g., DNA and/or DNA and RNA, thereby forming an eluate. The eluate is then contacted with a protein precipitation buffer that includes a transition metal and a buffering agent. The cfDNA and/or DNA and nucleic acids include at least the RNA from microvesicles is then isolated from the protein-precipitated eluate using any of a variety of art-recognized techniques, such as, for example, binding to a silica column followed by washing and elution.

In some embodiments, the elution buffer comprises a denaturing agent, a detergent, a buffer substance, and/or combinations thereof to maintain a defined solution pH. In some embodiments, the elution buffer includes a strong denaturing agent. In some embodiments, the elution buffer includes a strong denaturing agent and a reduction agent.

In some embodiments, the elution buffer contains guanidine thiocyanate (GTC), a denaturing agent that disrupts vesicle membranes, inactivates nucleases, and adjusts ionic strength for solid phase adsorption.

In some embodiments, the elution buffer contains a detergent such as, for example, Tween, Triton X-100, etc., to assist in the disruption of microvesicle membranes and to support efficient elution of the biomarkers from the capture surface.

In some embodiments, the elution buffer contains a reducing agent such as 13-Mercaptoethanol (BME), to reduce intramolecular disulfide bonds Cys-Cys and to assist in denaturing proteins especially RNases present in the eluate.

In some embodiments, the elution buffer contains GTC, a detergent, and a reducing agent.

In some embodiments, the transition metal ion in the protein precipitation buffer is zinc. In some embodiments, the zinc is present in the protein precipitation buffer as zinc chloride.

In some embodiments, the buffering agent in the protein precipitation buffer is sodium acetate (NaAc). In some embodiments, the buffering agent is NaAc at pH≤6.0.

In some embodiments, the protein precipitation buffer includes zinc chloride and NaAc buffering agent at pH≤6.0.

The membranes used in the methods and kits provided herein have large pores and are positively charged. In some embodiments, more than one membrane is used in the methods and kits, for example, two or more membranes are used. In some embodiments, three membranes are used. The number of membranes used in the methods and kits correlates with the total volume of sample that can be analyzed at one time. In some embodiments, about 1 ml of samples is processed for each layer of membrane used in the methods and kits.

In some embodiments, the membrane is a positively charged membrane. In some embodiments, the capture surface is an anion exchanger. In some embodiments, the capture surface is an anion exchanger with quaternary amines. In some embodiments, the capture surface is a Q membrane, which is a positively charged membrane and is an anion exchanger with quaternary amines. For example, the Q membrane is functionalized with quaternary ammonium, $R-CH_2-N^+(CH_3)_3$. In some embodiments, the membrane has a pore size that is at least 3 µm.

Purification of the sample, including the microvesicle fraction, is performed using ion exchange techniques. In some embodiments, the ion exchange technique is a technique selected from those shown in the working examples provided herein.

The methods provided herein provide efficient elution of the nucleic acids and/or protein biomarkers using an elution buffer composition that at least (i) allows for efficient lysis of extracellular vesicles and elution of the released nucleic acids; (ii) efficiently inhibits nucleases, such as, for example, RNases, and (iii) is of an ionic strength that is sufficient to allow for efficient absorption of the eluted nucleic acids to a solid phase, e.g., a silica membrane.

In one aspect, the method for extracting nucleic acids from a biological sample comprises (a) providing a biological sample; (b) contacting the biological sample with a capture surface under conditions sufficient to retain the microvesicle fraction on or in the capture surface; (c) lysing the microvesicle fraction while the microvesicles are on or in the capture surface; and (d) extracting the nucleic acids from the microvesicle fraction. Alternatively, the method for extracting nucleic acids from the biological sample further comprises eluting the microvesicle fraction from the capture surface after step (b), collecting the eluted microvesicle fraction, and extracting the nucleic acids from the eluted microvesicle fraction. Optionally, the eluted microvesicle fraction can be concentrated by a spin concentrator to obtain a concentrated microvesicle fraction, and the nucleic acids are subsequently extracted from the concentrated microvesicle fraction.

In some embodiments, the capture surface is a membrane. In one aspect, the membrane comprises regenerated cellulose. For example, the membrane has a pore size in the range of 3-5 µm. In another aspect, the membrane comprises polyethersulfone (PES). For example, the membrane has a pore size in the range of 20 nm to 0.8 um. In another aspect, the membrane is positively charged.

In some aspects, the membrane is functionalized. For example, the membrane is functionalized with quaternary ammonium R—$CH_2$—$N^+(CH_3)_3$.

In one embodiment, the capture surface comprises more than one membrane. In some embodiments, the capture surface comprises at least two membranes, wherein each membrane is adjacently next to the other membrane(s). In some embodiments, the capture surface comprises at least three membranes, wherein each of the three membranes is directly adjacent to one another. In some embodiments, the capture surface comprises at least four membranes, wherein each of the four membranes is directly adjacent to one another.

In some embodiments, the capture surface is a bead. For example, the bead is magnetic. Alternatively, the bead is non-magnetic. In yet another embodiment, the bead is functionalized with an affinity ligand.

The methods described herein provide for the extraction of nucleic acids from microvesicles. In some embodiments, the extracted nucleic acids are DNA and/or DNA and RNA. The extracted RNA may comprise messenger RNA, ribosomal RNA, transfer RNA, or small RNAs such as microRNAs, or any combination thereof.

Various nucleic acid sequencing techniques are used to detect and analyze nucleic acids such as cell free DNA and/or RNA extracted from the microvesicle fraction from biological samples. Analysis of nucleic acids such as cell free DNA and/or nucleic acids extracted from microvesicles for diagnostic purposes has wide-ranging implications due to the non-invasive nature in which microvesicles can be easily collected. Use of microvesicle analysis in place of invasive tissue biopsies will positively impact patient welfare, improve the ability to conduct longitudinal disease monitoring, and improve the ability to obtain expression profiles even when tissue cells are not easily accessible (e.g., in ovarian or brain cancer patients).

The biological sample is a bodily fluid. The bodily fluids can be fluids isolated from anywhere in the body of the subject, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. For example, the bodily fluid is urine, blood, serum, or cerebrospinal fluid.

In some embodiments, the biological sample is plasma. In some embodiments, the biological sample is serum. In some embodiments, the biological sample is urine. In some embodiments, the biological sample is cerebrospinal fluid. In some embodiments, the biological sample is cell culture supernatant.

Suitably a sample volume of about 0.1 ml to about 30 ml fluid may be used. The volume of fluid may depend on a few factors, e.g., the type of fluid used. For example, the volume of serum samples may be about 0.1 ml to about 4 ml, for example, about 0.2 ml to 4 ml. The volume of plasma samples may be about 0.1 ml to about 4 ml, for example, 0.5 ml to 4 ml. The volume of urine samples may be about 10 ml to about 30 ml, for example, about 20 ml.

In some aspects, the method described herein further comprises contacting the biological sample with a loading buffer. The loading buffer is in the range of pH 4-8. In one aspect, the loading buffer has a neutral pH.

In any of the foregoing methods, the nucleic acids are DNA and/or DNA and RNA. Examples of RNA include messenger RNAs, transfer RNAs, ribosomal RNAs, small RNAs (non-protein-coding RNAs, non-messenger RNAs), microRNAs, piRNAs, exRNAs, snRNAs and snoRNAs.

In any of the foregoing methods, the nucleic acids are isolated from or otherwise derived from a sample, including RNA isolated from the microvesicle fraction of a sample.

In any of the foregoing methods, the nucleic acids are cell-free nucleic acids, also referred to herein as circulating nucleic acids. In some embodiments, the cell-free nucleic acids are DNA or RNA.

Various aspects and embodiments of the invention will now be described in detail. It will be appreciated that modification of the details may be made without departing from the scope of the invention. Further, unless otherwise required by context, singular terms shall include pluralities and plural terms shall include the singular.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

BRIEF DESCRIPTION OF THE FIGURES

FIG. 1 is a schematic representation of the workflow for a method of the disclosure that isolates DNA and RNA from the sample.

DETAILED DESCRIPTION OF THE INVENTION

The present invention provides methods of isolating cell-free DNA (cfDNA) and/or cfDNA and nucleic acids including at least RNA from microvesicles by capturing the DNA and the microvesicles to a surface, subsequently lysing the microvesicles to release the nucleic acids, particularly RNA, contained therein, and eluting the DNA and/or DNA and nucleic acids including at least RNA from the capture surface. Microvesicles are shed by eukaryotic cells, or budded off of the plasma membrane, to the exterior of the cell. These membrane vesicles are heterogeneous in size with diameters ranging from about 10 nm to about 5000 nm. All membrane vesicles shed by cells<0.8 μm in diameter are referred to herein collectively as "microvesicles." These microvesicles include microvesicles, microvesicle-like particles, prostasomes, dexosomes, texosomes, ectosomes, oncosomes, apoptotic bodies, retrovirus-like particles, and human endogenous retrovirus (HERV) particles. Small microvesicles (approximately 10 to 1000 nm, and more often 30 to 200 nm in diameter) that are released by exocytosis of intracellular multivesicular bodies are referred to in the art as "microvesicles."

The methods and kits isolate and extract nucleic acids, e.g., DNA and/or DNA and nucleic acids including at least RNA from a sample using the following general procedure. First, the nucleic acids in the sample, e.g., the DNA and/or the DNA and the microvesicle fraction, are bound to a capture surface such as a membrane filter, and the capture surface is washed. Then, an elution reagent is used to perform on-membrane lysis and release of the nucleic acids, e.g., DNA and/or DNA and RNA, thereby forming an eluate. The eluate is then contacted with a protein precipitation buffer that includes a transition metal and a buffering agent. The cfDNA and/or DNA and nucleic acids include at least the RNA from microvesicles is then isolated from the protein-precipitated eluate using any of a variety of art-recognized techniques, such as, for example, binding to a silica column followed by washing and elution.

In some embodiments, the elution buffer comprises a denaturing agent, a detergent, a buffer substance, and/or combinations thereof to maintain a defined solution pH. In some embodiments, the elution buffer includes a strong denaturing agent. In some embodiments, the elution buffer includes a strong denaturing agent and a reduction agent.

In some embodiments, the elution buffer contains guanidine thiocyanate (GTC), a denaturing agent that disrupts vesicle membranes, inactivates nucleases, and adjusts ionic strength for solid phase adsorption.

In some embodiments, the elution buffer contains a detergent such as, for example, Tween, Triton X-100, etc., to assist in the disruption of microvesicle membranes and to support efficient elution of the biomarkers from the capture surface.

In some embodiments, the elution buffer contains a reducing agent such as 13-Mercaptoethanol (BME), to reduce intramolecular disulfide bonds Cys-Cys and to assist in denaturing proteins especially RNases present in the eluate.

In some embodiments, the elution buffer contains GTC, a detergent, and a reducing agent.

In some embodiments, the transition metal ion in the protein precipitation buffer is zinc. In some embodiments, the zinc is present in the protein precipitation buffer as zinc chloride.

In some embodiments, the buffering agent in the protein precipitation buffer is sodium acetate (NaAc). In some embodiments, the buffering agent is NaAc at pH≤6.0.

In some embodiments, the protein precipitation buffer includes zinc chloride and NaAc buffering agent at pH≤6.0.

Current methods of isolating DNA and/or DNA and nucleic acids including at least RNA from microvesicles include hazardous substances, ultracentrifugation, ultrafiltration, e.g., using 100 kD filters, polymer precipitation techniques, and/or filtration based on size. However, there exists a need for alternative methods that are efficient and effective for isolating microvesicles and, optionally, extracting the nucleic acids contained therein, for example, in some embodiments, microvesicle RNA, for use in a variety of applications, including diagnostic purposes.

The isolation and extraction methods and/or kits provided herein use a spin-column based purification process using an affinity membrane that binds cell free DNA and/or microvesicles. The methods and kits of the disclosure allow for the capability to run large numbers of clinical samples in parallel, using volumes from 0.2 up to 4 mL on a single column. The cell-free DNA isolated using the procedures provided herein is highly pure. The isolated RNA is highly pure, protected by a vesicle membrane until lysis, and intact vesicles can be eluted from the membrane. The procedure is able to deplete substantially all cell-free DNA from plasma input, and is equal to or better in DNA yield when compared to commercially available circulating DNA isolation kits. The procedure is able to deplete substantially all mRNA from plasma input, and is equal or better in mRNA/miRNA yield when compared to ultracentrifugation or direct lysis. In contrast to commercially available kits and/or previous isolation methods, the methods and/or kits enrich for the microvesicle bound fraction of miRNAs, and they are easily scalable to large amounts of input material. This ability to scale up enables research on interesting, low abundant transcripts. In comparison with other commercially available products on the market, the methods and kits of the disclosure provide unique capabilities that are demonstrated by the examples provided herein.

The methods and kits isolate and extract nucleic acids, e.g., DNA and/or DNA and nucleic acids including at least RNA from a biological sample using the following general procedure. First, the sample, including the cfDNA and the microvesicle fraction, is bound to a membrane filter, and the filter is washed. Then, a GTC-based reagent is used to perform on-membrane lysis and release of the nucleic acids, e.g., DNA and/or DNA and RNA. Protein precipitation is then performed. The nucleic acids, e.g., DNA and/or DNA and RNA, is then bound to a silica column, washed and then eluted. The extracted nucleic acids, e.g., DNA and/or DNA and RNA, can then be further analyzed, for example, using any of a variety of downstream assays.

In some embodiments, the method includes the following steps. The filter is contained in spin column. Prior to addition of the lysis reagent, the sample is bound to a membrane filter in a spin column, and the spin column is then spun for 1 min at approximately 500×g. The flow-through is then discarded, a buffer is added to the spin column, and the spin column is spun again for 5 min at approximately 5000×g to remove residual volume from the column. The flow-through is discarded after this second spin. The spin column is then contacted with the GTC-based lysis reagent and spun for 5 min at approximately 5000×g to collect the homogenate containing the lysed microvesicles and captured cfDNA. In some embodiments, the lysis buffer is a GTC-based lysis buffer. The homogenate is then subject to nucleic acid isolation and extraction. In some embodiments, a control for RNA isolation efficiency, such as, for example, Q-beta or any other control described herein, is spiked-in to the homogenate prior to nucleic acid isolation and extraction.

In some embodiments, the nucleic acid is isolated according to the following steps. After addition of the lysis reagent, a protein precipitation buffer is then added to the homogenate, and the solution is mixed vigorously for a brief time period. The solution is then centrifuged for 3 min at 12,000×g at room temperature. The solution can then be processed using any of a variety of art-recognized methods for isolating and/or extracting nucleic acids.

The isolated nucleic acids, e.g., DNA and/or DNA and RNA, can then be subject to further analysis using any of a variety of downstream assays. In some embodiments, the combined detection of DNA and RNA is used to increase the sensitivity for actionable mutations. There are multiple potential sources of detectable mutations in circulating nucleic acids. For example, living tumor cells are a potential source for RNA and DNA isolated from the microvesicle fraction of a sample, and dying tumor cells are potential sources for cell-free DNA sources such as, for example, apoptotic vesicle DNA and cell-free DNA from necrotic tumor cells. As mutated nucleic acids are relatively infrequent in circulation, the maximization of detection sensitivity becomes very important. Combined isolation of DNA and RNA delivers comprehensive clinical information to assess progression of disease and patient response to therapy. However, in contrast to the methods and kits provided herein, commercially available kits for detecting circulating nucleic acids are only able to isolate cfDNA from plasma, i.e., from dying cells. Those of ordinarily skill in the art will appreciate that more copies of a mutation or other biomarker leads to enhanced sensitivity and accuracy in identifying mutations and other biomarkers.

The methods of the disclosure can be used to isolate all DNA from plasma samples. The methods of the disclosure separate RNA and DNA at similar levels for the same sample volume, and the RNA and DNA can be separated from each other. These methods of the disclosure capture the same or more cell-free DNA (cfDNA), the same or more mRNA and much more miRNA than a commercially available isolation kit.

The methods of the disclosure can also be used for co-purification of RNA and DNA. The methods of the disclosure (also referred to herein as procedures) can be used to isolate RNA and DNA from exosomes and other microvesicles using 0.2-4 mL of plasma or serum. The list of compatible plasma tubes includes plasma with the additives EDTA, sodium citrate, and citrate-phosphate-dextrose. Plasma containing heparin can inhibit RT-qPCR.

The sample, alone or diluted with a binding buffer, is then loaded onto the spin column having a capture membrane and spun for 1 min at 500×g. The flow-through is discarded, and the column is then placed back into the same collection tube. Wash buffer is then added and the column is spun for 5 min at 5000×g to remove residual volume from the column. Note: After centrifugation, the spin column is removed from the collection tube so that the column does not contact the flow-through. The spin column is then transferred to a fresh collection tube, and the GTC-based elution buffer is added to the membrane. Then, the spin column is spun for 5 min at 5000×g to collect the homogenate containing the lysed exosomes. Protein precipitation is then performed.

The methods provided herein are useful for isolating and detecting DNA from biological samples. Vesicle RNA is thought to be derived from living cells in e.g. the diseased tissue. Cell-free DNA cfDNA) is thought to be derived from dying cells e.g. necrotic cells in the disease tissue. Thus, cfDNA is useful as an indicator of therapeutic response, while the RNA is an indicator of resistance mutations on the rise.

The methods provided herein are useful for detection of rare mutations in blood, as the method provides a sufficiently sensitive method that can be applied on nucleic acids of sufficient amount. The amount of actual DNA and RNA molecules in biofluids is very limited, and the methods provide an isolation method that extracts all molecules of the blood that are relevant for mutation detection in a volume small enough for effective downstream processing and/or analysis.

As used herein, the term "nucleic acids" refer to DNA and RNA. The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements.

As used herein, the term "biological sample" refers to a sample that contains biological materials such as DNA, RNA and protein.

In some embodiments, the biological sample may suitably comprise a bodily fluid from a subject. The bodily fluids can be fluids isolated from anywhere in the body of the subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

In some embodiments, the biological sample may suitably comprise cell culture supernatant.

In some embodiments, the biological sample may suitably comprise a tissue sample from a subject. The tissue sample can be isolated from anywhere in the body of the subject.

A suitable sample volume of a bodily fluid is, for example, in the range of about 0.1 ml to about 30 ml fluid. The volume of fluid may depend on a few factors, e.g., the type of fluid used. For example, the volume of serum samples may be about 0.1 ml to about 4 ml, for example, in some embodiments, about 0.2 ml to 4 ml. The volume of plasma samples may be about 0.1 ml to about 4 ml, for example, in some embodiments, 0.5 ml to 4 ml. The volume of urine samples may be about 10 ml to about 30 ml, for example, in some embodiments, about 20 ml.

While the examples provided herein used plasma samples, the skilled artisan will appreciate that these methods are applicable to a variety of biological samples.

The methods and kits of the disclosure are suitable for use with samples derived from a human subject. The methods and kits of the disclosure are suitable for use with samples derived from a human subject. In addition, the methods and kits of the disclosure are also suitable for use with samples derived from a human subject. The methods and kits of the disclosure are suitable for use with samples derived from a non-human subject such as, for example, a rodent, a nonhuman primate, a companion animal (e.g., cat, dog, horse), and/or a farm animal (e.g., chicken).

The term "subject" is intended to include all animals shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig. Etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject," "patient," and "individual" are used interchangeably herein.

While the working examples provided herein use a membrane as the capture surface, it should be understood that the format of the capturing surface, e.g., beads or a filter (also referred to herein as a membrane), does not affect the ability of the methods provided herein to efficiently capture microvesicles from a biological sample.

A wide range of surfaces are capable of capturing microvesicles according to the methods provided herein, but not all surfaces will capture microvesicles (some surfaces do not capture anything).

The present disclosure also describes a device for isolating and concentrating microvesicles from biological or clinical samples using disposable plastic parts and centrifuge equipment. For example, the device comprises a column comprising a capture surface (i.e., a membrane filter), a holder that secures the capture surface between the outer frit and an inner tube, and a collection tube. The outer frit comprises a large net structure to allow passing of liquid, and is preferably at one end of the column. The inner tube holds the capture surface in place, and preferably is slightly conus-shaped. The collection tube may be commercially available, i.e., 50 ml Falcon tube. The column is preferably suitable for spinning, i.e., the size is compatible with standard centrifuge and micro-centrifuge machines.

In embodiments where the capture surface is a membrane, the device for isolating the microvesicle fraction from a biological sample contains at least one membrane. In some embodiments, the device comprises one, two, three, four, five or six membranes. In some embodiments, the device comprises three membranes. In embodiments where the device comprises more than one membrane, the membranes are all directly adjacent to one another at one end of the column. In embodiments where the device comprises more than one membrane, the membranes are all identical to each other, i.e., are of the same charge and/or have the same functional group.

It should be noted that capture by filtering through a pore size smaller than the microvesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use any of a variety of capture surfaces. In some embodiments, the capture surface is a membrane, also referred to herein as a filter or a membrane filter. In some embodiments, the capture surface is a commercially available membrane. In some embodiments, the capture surface is a charged commercially available membrane. In some embodiments, the capture surface is neutral. In some embodiments, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In embodiments where the capture surface is charged, the capture surface can be a charged filter selected from the group consisting of 0.65 um positively charged Q PES vacuum filtration (Millipore), 3-5 um positively charged Q RC spin column filtration (Sartorius), 0.8 um positively charged Q PES homemade spin column filtration (Pall), 0.8 um positively charged Q PES syringe filtration (Pall), 0.8 um negatively charged S PES homemade spin column filtration (Pall), 0.8 um negatively charged S PES syringe filtration (Pall), and 50 nm negatively charged nylon syringe filtration (Sterlitech). In some embodiments, the charged filter is not housed in a syringe filtration apparatus, as nucleic acid can be harder to get out of the filter in these embodiments. In some embodiments, the charged filter is housed at one end of a column.

In embodiments where the capture surface is a membrane, the membrane can be made from a variety of suitable materials. In some embodiments, the membrane is polyethersulfone (PES) (e.g., from Millipore or PALL Corp.). In some embodiments, the membrane is regenerated cellulose (RC) (e.g., from Sartorius or Pierce).

In some embodiments, the capture surface is a positively charged membrane. In some embodiments, the capture surface is a Q membrane, which is a positively charged membrane and is an anion exchanger with quaternary amines. For example, the Q membrane is functionalized with quaternary ammonium, $R-CH_2-N^+(CH_3)_3$. In some embodiments, the capture surface is a negatively charged membrane. In some embodiments, the capture surface is an S membrane, which is a negatively charged membrane and is a cation exchanger with sulfonic acid groups. For example, the S membrane is functionalized with sulfonic acid, $R-CH_2-SO_3^-$. In some embodiments, the capture surface is a D membrane, which is a weak basic anion exchanger with diethylamine groups, $R-CH_2-NH^+(C_2H_5)_2$. In some embodiments, the capture surface is a metal chelate membrane. For example, the membrane is an IDA membrane, functionalized with minodiacetic acid $-N(CH_2COOH^-)_2$. In some embodiments, the capture surface is a microporous membrane, functionalized with aldehyde groups, $-CHO$. In other embodiments, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In embodiments where the capture surface is charged, microvesicles can be isolated with a positively charged filter.

In embodiments where the capture surface is charged, the pH during microvesicle capture is a pH≤7. In some embodiments, the pH is greater than 4 and less than or equal to 8.

In embodiments where the capture surface is a positively charged Q filter, the buffer system includes a wash buffer comprising 250 mM Bis Tris Propane, pH6.5-7.0. In embodiments where the capture surface is a positively charged Q filter, the lysis buffer is a GTC-based reagent. In embodiments where the capture surface is a positively charged Q filter, the lysis buffer is present at one volume. In embodiments where the capture surface is a positively charged Q filter, the lysis buffer is present at more than one volume.

Depending on the membrane material, the pore sizes of the membrane range from 3 μm to 20 nm.

The surface charge of the capture surface can be positive, negative or neutral. In some embodiments, the capture surface is a positively charged bead or beads.

The methods provided herein include a lysis reagent. In some embodiments, the agent used for on-membrane lysis is a GTC-based reagent. In some embodiments, the lysis reagent is a high salt based buffer.

The methods provided herein include a variety of buffers including loading and wash buffers. Loading and wash buffers can be of high or low ionic strength. The salt concentration, e.g., NaCl concentration, can be from 0 to 2.4M. The buffers can include a variety of components. In some embodiments, the buffers include one or more of the following components: Tris, Bis-Tris, Bis-Tris-Propane, Imidazole, Citrate, Methyl Malonic Acid, Acetic Acid, Ethanolamine, Diethanolamine, Triethanolamine (TEA) and Sodium phosphate. In the methods provided herein, the pH of loading and wash buffers is important. Filters tend to clog when plasma samples at set to pH≤5.5 before loading (the plasma will not spin through the column at all), and at higher pH microvesicle RNA recovery is lower due to instability of the microvesicles. At neutral pH, the RNA recovery from microvesicles is optimal. In some embodiments, the buffer used is at 1× concentration, 2× concentration, 3× concentration, or 4× concentration. For example, the loading or binding buffer is at 2× concentration while the wash buffer is at 1× concentration.

In some embodiments, the methods include one or more wash steps, for example, after contacting the biological sample with the capture surface. In some embodiments, detergents are added to the wash buffer to facilitate removing the non-specific binding (i.e., contaminants, cell debris, and circulating protein complexes or nucleic acids), to obtain a more pure microvesicle fraction. Detergents suitable for use include, but are not limited to, sodium dodecyl sulfate (SDS), Tween-20, Tween-80, Triton X-100, Nonidet P-40 (NP-40), Brij-35, Brij-58, octyl glucoside, octyl thioglucoside, CHAPS or CHAPSO.

In some embodiments, the capture surface, e.g., membrane, is housed within a device used for centrifugation; e.g. spin columns, or for vacuum system e.g. vacuum filter holders, or for filtration with pressure e.g. syringe filters. In some embodiments, the capture surface is housed in a spin column or vacuum system.

The isolation of microvesicles from a biological sample prior to extraction of nucleic acids is advantageous for the following reasons: 1) extracting nucleic acids from microvesicles provides the opportunity to selectively analyze disease or tumor-specific nucleic acids obtained by isolating disease or tumor-specific microvesicles apart from other microvesicles within the fluid sample; 2) nucleic acid-containing microvesicles produce significantly higher yields of nucleic acid species with higher integrity as compared to the yield/integrity obtained by extracting nucleic acids directly from the fluid sample without first isolating microvesicles; 3) scalability, e.g., to detect nucleic acids expressed at low levels, the sensitivity can be increased by concentrating microvesicles from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; and 5) more choices in nucleic acid extraction methods can be utilized as isolated microvesicle fractions can be of a smaller volume than that of the starting sample volume, making it possible to extract nucleic acids from these fractions or pellets using small volume column filters.

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

An object of the present invention is therefore to provide a method for quick and easy isolation of nucleic acid-containing particles from biological samples such as body fluids and extraction of high quality nucleic acids from the isolated particles. The method of the invention may be suitable for adaptation and incorporation into a compact device or instrument for use in a laboratory or clinical setting, or in the field.

In some embodiments, the sample is not pre-processed prior to isolation and extraction of nucleic acids, e.g., DNA and/or DNA and RNA, from the biological sample.

In some embodiments, the sample is subjected to a pre-processing step prior to isolation, purification or enrichment of the microvesicles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof. Where more than one centrifugation pre-processing steps are performed, the biological sample may be centrifuged first at the lower speed and then at the higher speed. If desired, further suitable centrifugation pre-processing steps may be carried out. Alternatively or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 μm filter.

In some embodiments, the sample is pre-filtered to exclude particles larger than 0.8 μm. In some embodiments, the sample includes an additive such as EDTA, sodium citrate, and/or citrate-phosphate-dextrose. In some embodiments, the sample does not contain heparin, as heparin can negatively impact RT-qPCR and other nucleic acid analysis. In some embodiments, the sample is mixed with a buffer prior to purification and/or nucleic acid isolation and/or extraction. In some embodiments, the buffer is a binding buffer.

In some embodiments, one or more centrifugation steps are performed before or after contacting the biological sample with the capture surface to separate microvesicles and concentrate the microvesicles isolated from the biological fraction. For example, the sample is centrifuged at 20,000 g for 1 hour at 4° C. To remove large unwanted particles, cells, and/or cell debris, the samples may be centrifuged at a low speed of about 100-500 g, for example, in some embodiments, about 250-300 g. Alternatively or in addition, the samples may be centrifuged at a higher speed. Suitable centrifugation speeds are up to about 200,000 g, for example from about 2,000 g to less than about 200,000 g. Speeds of above about 15,000 g and less than about 200,000 g or above about 15,000 g and less than about 100,000 g or above about 15,000 g and less than about 50,000 g are used in some embodiments. Speeds of from about 18,000 g to about 40,000 g or about 30,000 g; and from about 18,000 g to about 25,000 g are more preferred. In some embodiments, a centrifugation speed of about 20,000 g. Generally, suitable times for centrifugation are from about 5 minutes to about 2 hours, for example, from about 10 minutes to about 1.5 hours, or from about 15 minutes to about 1 hour. A time of about 0.5 hours may be used. It is sometimes useful, in some embodiments, to subject the biological sample to centrifugation at about 20,000 g for about 0.5 hours. However the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., for example, about 1-5° C., e.g., about 3° C. or about 4° C.

In some embodiments, one or more filtration steps are performed before or after contacting the biological sample with the capture surface. A filter having a size in the range about 0.1 to about 1.0 μm may be employed, for example, about 0.8 μm or 0.22 μm. The filtration may also be performed with successive filtrations using filters with decreasing porosity.

In some embodiments, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the microvesicles. This may consist of a series of differential centrifugations. The microvesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the microvesicle fraction. In another embodiment, the filtration is an ultrafiltration, for example, a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the invention, the use of membranes with a cut-off threshold below 1000 kDa, for example, in some embodiments, between 100 kDa and 1000 kDa, or for example, in some embodiments, between 100 kDa and 600 kDa, is advantageous.

In some embodiments, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are used in some embodiments. For example, such supports include, but are not limited to: SUPERDEX® 200HR (Pharmacia), TSK G6000 (TosoHaas) or SEP-HACRYL® S (Pharmacia).

In some embodiments, one or more affinity chromatography steps are performed before or after contacting the biological sample with the capture surface. Some microvesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of long, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

In some embodiments, one or more control particles or one or more nucleic acid(s) may be added to the sample prior to microvesicle isolation and/or nucleic acid extraction to serve as an internal control to evaluate the efficiency or quality of microvesicle purification and/or nucleic acid extraction. The methods described herein provide for the efficient isolation and the control nucleic acid(s) along with the microvesicle fraction. These control nucleic acid(s) include one or more nucleic acids from Q-beta bacteriophage, one or more nucleic acids from a virus particles, or any other control nucleic acids (e.g., at least one control target gene) that may be naturally occurring or engineered by recombinant DNA techniques. In some embodiments, the quantity of control nucleic acid(s) is known before the addition to the sample. The control target gene can be quantified using real-time PCR analysis. Quantification of a control target gene can be used to determine the efficiency or quality of the microvesicle purification or nucleic acid extraction processes.

In some embodiments, the control nucleic acid is a nucleic acid from a Q-beta bacteriophage, referred to herein as "Q-beta control nucleic acid." The Q-beta control nucleic acid used in the methods described herein may be a naturally-occurring virus control nucleic acid or may be a recombinant or engineered control nucleic acid. Q-beta is a member of the leviviridae family, characterized by a linear, single-stranded RNA genome that consists of 3 genes encoding four viral proteins: a coat protein, a maturation protein, a lysis protein, and RNA replicase. When the Q-beta particle itself is used as a control, due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. When the Q-beta particle itself is used as a control, after addition of the Q-beta particles to the biological sample, the nucleic acids from the Q-beta particle are extracted along with the nucleic acids from the biological sample using the extraction methods described herein. When a nucleic acid from Q-beta, for example, RNA from Q-beta, is used as a control, the Q-beta nucleic acid is extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added or the copy number detected and the quantity of Q-beta nucleic acid, for example, Q-beta RNA, added can be compared to determine the quality of the isolation and/or extraction process.

In some embodiments, 50, 100, 150, 200, 250, 300, 350, 400, 450, 500, 1,000 or 5,000 copies of Q-beta particles or Q-beta nucleic acid, for example, Q-beta RNA, added to a bodily fluid sample. In some embodiments, 100 copies of Q-beta particles or Q-beta nucleic acid, for example, Q-beta RNA, are added to a bodily fluid sample. When the Q-beta particle itself is used as control, the copy number of Q-beta particles can be calculated based on the ability of the Q-beta bacteriophage to infect target cells. Thus, the copy number of Q-beta particles is correlated to the colony forming units of the Q-beta bacteriophage.

Optionally, control particles may be added to the sample prior to microvesicle isolation or nucleic acid extraction to serve as an internal control to evaluate the efficiency or quality of microvesicle purification and/or nucleic acid extraction. The methods described herein provide for the efficient isolation and the control particles along with the microvesicle fraction. These control particles include Q-beta bacteriophage, virus particles, or any other particle that contains control nucleic acids (e.g., at least one control target gene) that may be naturally occurring or engineered by recombinant DNA techniques. In some embodiments, the quantity of control particles is known before the addition to the sample. The control target gene can be quantified using real-time PCR analysis. Quantification of a control target gene can be used to determine the efficiency or quality of the microvesicle purification or nucleic acid extraction processes.

In some embodiments, the control particle is a Q-beta bacteriophage, referred to herein as "Q-beta particle." The Q-beta particle used in the methods described herein may be a naturally-occurring virus particle or may be a recombinant or engineered virus, in which at least one component of the virus particle (e.g., a portion of the genome or coat protein) is synthesized by recombinant DNA or molecular biology techniques known in the art. Q-beta is a member of the leviviridae family, characterized by a linear, single-stranded RNA genome that consists of 3 genes encoding four viral proteins: a coat protein, a maturation protein, a lysis protein, and RNA replicase. Due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. After addition of the Q-beta particles to the biological sample, the nucleic acids from the Q-beta particle are extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added can be compared to determine the quality of the isolation and/or extraction process.

In some embodiments, the Q-beta particles are added to the urine sample prior to nucleic extraction. For example, the Q-beta particles are added to the urine sample prior to ultrafiltration and/or after the pre-filtration step.

In some embodiments, the methods and kits described herein include one or more in-process controls. In some embodiments, the in-process control is detection and analysis of a reference gene that indicates sample quality (i.e., an indicator of the quality of the biological sample, e.g., biofluid sample). In some embodiments, the in-process control is detection and analysis of a reference gene that indicates plasma quality (i.e., an indicator of the quality of the plasma sample). In some embodiments, the reference gene(s) is/are analyzed by additional qPCR.

In some embodiments, the in-process control is an in-process control for reverse transcriptase and/or PCR performance. These in-process controls include, by way of non-limiting examples, a reference RNA (also referred to herein as ref.RNA), that is spiked in after RNA isolation and prior to reverse transcription. In some embodiments, the ref.RNA is a control such as Qbeta. In some embodiments, the ref.RNA is analyzed by additional PCR.

Nucleic Acid Extraction

The present invention is directed towards the use of a capture surface for the improved isolation, purification, or enrichment of microvesicles. The methods disclosed herein provide a highly enriched microvesicle fraction for extraction of high quality nucleic acids from said microvesicles. The nucleic acid extractions obtained by the methods described herein may be useful for various applications in which high quality nucleic acid extractions are required or preferred, such as for use in the diagnosis, prognosis, or monitoring of diseases or medical conditions.

Recent studies reveal that nucleic acids within microvesicles have a role as biomarkers. For example, WO 2009/100029 describes, among other things, the use of nucleic acids extracted from microvesicles in GBM patient serum for medical diagnosis, prognosis and therapy evaluation. WO 2009/100029 also describes the use of nucleic acids extracted from microvesicles in human urine for the same purposes. The use of nucleic acids extracted from microvesicles is considered to potentially circumvent the need for biopsies, highlighting the enormous diagnostic potential of microvesicle biology (Skog et al., 2008).

The quality or purity of the isolated microvesicles can directly affect the quality of the extracted microvesicle nucleic acids, which then directly affects the efficiency and sensitivity of biomarker assays for disease diagnosis, prognosis, and/or monitoring. Given the importance of accurate and sensitive diagnostic tests in the clinical field, methods for isolating highly enriched microvesicle fractions from biological samples are needed. To address this need, the present invention provides methods for isolating microvesicles from biological sample for the extraction of high quality nucleic acids from a biological sample. As shown herein, highly enriched microvesicle fractions are isolated from biological samples by methods described herein, and wherein high quality nucleic acids subsequently extracted from the highly enriched microvesicle fractions. These high quality extracted nucleic acids are useful for measuring or assessing the presence or absence of biomarkers for aiding in the diagnosis, prognosis, and/or monitoring of diseases or other medical conditions.

As used herein, the term "high quality" in reference to nucleic acid extraction means an extraction in which one is able to detect 18S and 28S rRNA, for example, in some embodiments, in a ratio of approximately 1:1 to approximately 1:2; and/or for example, in some embodiments, approximately 1:2. Ideally, high quality nucleic acid extractions obtained by the methods described herein will also have an RNA integrity number of greater than or equal to 5 for a low protein biological sample (e.g., urine), or greater than or equal to 3 for a high protein biological sample (e.g., serum), and a nucleic acid yield of greater than or equal to 50 pg/ml from a 20 ml low protein biological sample or a 1 ml high protein biological sample.

High quality RNA extractions are desirable because RNA degradation can adversely affect downstream assessment of the extracted RNA, such as in gene expression and mRNA analysis, as well as in analysis of non-coding RNA such as small RNA and microRNA. The new methods described herein enable one to extract high quality nucleic acids from microvesicles isolated from a biological sample so that an accurate analysis of nucleic acids within the microvesicles can be performed.

Following the isolation of microvesicles from a biological sample, nucleic acid may be extracted from the isolated or enriched microvesicle fraction. To achieve this, in some embodiments, the microvesicles may first be lysed. The lysis of microvesicles and extraction of nucleic acids may be achieved with various methods known in the art, including those described in PCT Publication Nos. WO 2016/007755 and WO 2014/107571, the contents of each of which are hereby incorporated by reference in their entirety. In some embodiments, the nucleic acid extraction may be achieved using protein precipitation according to standard procedures and techniques known in the art. Such methods may also utilize a nucleic acid-binding column to capture the nucleic acids contained within the microvesicles. Once bound, the nucleic acids can then be eluted using a buffer or solution suitable to disrupt the interaction between the nucleic acids and the binding column, thereby successfully eluting the nucleic acids.

In some embodiments, the nucleic acid extraction methods also include the step of removing or mitigating adverse factors that prevent high quality nucleic acid extraction from a biological sample. Such adverse factors are heterogeneous in that different biological samples may contain various species of adverse factors. Tn some biological samples, factors such as excessive DNA may affect the quality of nucleic acid extractions from such samples. In other samples, factors such as excessive endogenous Rnase may affect the quality of nucleic acid extractions from such samples. Many agents and methods may be used to remove these adverse factors. These methods and agents are referred to collectively herein as an "extraction enhancement operations." Tn some instances, the extraction enhancement operation may involve the addition of nucleic acid extraction enhancement agents to the biological sample. To remove adverse factors such as endogenous Rnases, such extraction enhancement agents as defined herein may include, but are not limited to, an Rnase inhibitor such as Superase-In (commercially available from Ambion Inc.) or RnaseINplus (commercially available from Promega Corp.), or other agents that function in a similar fashion; a protease (which may function as an Rnase inhibitor); Dnase; a reducing agent; a decoy substrate such as a synthetic RNA and/or carrier RNA; a soluble receptor that can bind Rnase; a small interfering RNA (siRNA); an RNA binding molecule, such as an anti-RNA antibody, a basic protein or a chaperone protein; an Rnase denaturing substance, such as a high osmolarity solution, a detergent, or a combination thereof.

For example, the extraction enhancement operation may include the addition of an Rnase inhibitor to the biological sample, and/or to the isolated microvesicle fraction, prior to extracting nucleic acid; for example, in some embodiments, the Rnase inhibitor has a concentration of greater than 0.027 AU (Ix) for a sample equal to or more than 1 µl in volume; alternatively, greater than or equal to 0.1 35 AU (5×) for a sample equal to or more than 1 µl; alternatively, greater than or equal to 0.27 AU (10×) for a sample equal to or more than 1 µl; alternatively, greater than or equal to 0.675 AU (25×) for a sample equal to or more than 1 µl; and alternatively, greater than or equal to 1.35 AU (50×) for a sample equal to or more than 1 µl; wherein the Ix concentration refers to an enzymatic condition wherein 0.027 AU or more Rnase inhibitor is used to treat microvesicles isolated from 1 or more bodily fluid, the 5× concentration refers to an enzymatic condition wherein 0.135 AU or more Rnase inhibitor is used to treat microvesicles isolated from 1 µl or more bodily fluid, the 10× protease concentration refers to an enzymatic condition wherein 0.27 AU or more Rnase inhibitor is used to treat particles isolated from 1 µl or more bodily fluid, the 25× concentration refers to an enzymatic condition wherein 0.675 AU or more Rnase inhibitor is used to treat microvesicles isolated from 1 µl or more bodily fluid, and the 50× protease concentration refers to an enzymatic condition wherein 1.35 AU or more Rnase inhibitor is used to treat particles isolated from 1 µl or more bodily fluid. In some embodiments, the Rnase inhibitor is a protease, in which case, 1 AU is the protease activity that releases folin-positive amino acids and peptides corresponding to 1 µmol tyrosine per minute.

These enhancement agents may exert their functions in various ways, e.g., through inhibiting Rnase activity (e.g., Rnase inhibitors), through a ubiquitous degradation of proteins (e.g., proteases), or through a chaperone protein (e.g., a RNA-binding protein) that binds and protects RNAs. In all instances, such extraction enhancement agents remove or at least mitigate some or all of the adverse factors in the biological sample or associated with the isolated particles that would otherwise prevent or interfere with the high quality extraction of nucleic acids from the isolated particles.

In some embodiments, the quantification of 18S and 28S rRNAs extracted can be used determine the quality of the nucleic acid extraction.

Detection of Nucleic Acid Biomarkers

In some embodiments, the extracted nucleic acid comprises DNA and/or DNA and RNA. In embodiments where the extracted nucleic acid comprises DNA and RNA, the RNA is reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample).

In another embodiment, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

In some embodiments, one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated microvesicles, whether wild type or variants, are identified with methods known in the art.

The present invention also includes various uses of the new methods of isolating microvesicles from a biological sample for high quality nucleic acid extraction from a for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

In some embodiments, it may be beneficial or otherwise desirable to amplify the nucleic acid of the microvesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a genetic or expression profile.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In other embodiment, the step of nucleic acid amplification is not performed. Instead, the extract nucleic acids are analyzed directly (e.g., through next-generation sequencing).

The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE)(Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et at, 1995; Landegren et al., 1988; Nakazawa et al., 1994), flow-cytometric heteroduplex analysis (WO/2006/113590) and combinations/modifications thereof. Notably, gene expression levels may be determined by the serial analysis of gene expression (SAGE) technique (Velculescu et al., 1995). In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teaching of these methods.

Many biomarkers may be associated with the presence or absence of a disease or other medical condition in a subject. Therefore, detection of the presence or absence of a biomarker or combination of biomarkers in a nucleic acid extraction from isolated particles, according to the methods disclosed herein, aid diagnosis of a disease or other medical condition in the subject.

Further, many biomarkers may help disease or medical status monitoring in a subject. Therefore, the detection of the presence or absence of such biomarkers in a nucleic acid extraction from isolated particles, according to the methods disclosed herein, may aid in monitoring the progress or reoccurrence of a disease or other medical condition in a subject.

Many biomarkers have also been found to influence the effectiveness of treatment in a particular patient. Therefore, the detection of the presence or absence of such biomarkers in a nucleic acid extraction from isolated particles, according to the methods disclosed herein, may aid in evaluating the efficacy of a given treatment in a given patient. The identification of these biomarkers in nucleic acids extracted from isolated particles from a biological sample from a patient may guide the selection of treatment for the patient.

In certain embodiments of the foregoing aspects of the invention, the disease or other medical condition is a neoplastic disease or condition (e.g., cancer or cell proliferative disorder).

In some embodiments, the extracted nucleic acids, e.g., exoRNA, are further analyzed based on detection of a biomarker or a combination of biomarkers. In some embodiments, the further analysis is performed using machine-learning based modeling, data mining methods, and/or statistical analysis. In some embodiments, the data is analyzed to identify or predict disease outcome of the patient. In some embodiments, the data is analyzed to stratify the patient within a patient population. In some embodiments, the data is analyzed to identify or predict whether the patient is resistant to treatment. In some embodiments, the data is used to measure progression-free survival progress of the subject.

In some embodiments, the data is analyzed to select a treatment option for the subject when a biomarker or combination of biomarkers is detected. In some embodiments, the treatment option is treatment with a combination of therapies.

Kits for Isolating Microvesicles from a Biological Sample

One aspect of the present invention is further directed to kits for use in the methods disclosed herein. The kit comprises a capture surface apparatus sufficient to separate microvesicles from a biological sample from unwanted particles, debris, and small molecules that are also present in the biological sample. The present invention also optionally includes instructions for using the foregoing reagents in the isolation and optional subsequent nucleic acid extraction process.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method for extracting DNA and RNA from a biological sample comprising:
   (a) contacting the biological sample with a solid capture surface and a chemical crowding agent, thereby retaining cell-free DNA and microvesicles from the biological sample on or in the capture surface, wherein the chemical crowding agent comprises polyethylene glycol, wherein the solid capture surface comprises at least one anion exchange membrane or at least one anion exchange bead;
   (b) contacting the capture surface with a guanidine thiocyanate-based elution buffer while cell-free DNA and the microvesicles are on or in the capture surface, thereby releasing the DNA and RNA from the sample and producing a homogenate; and
   (c) contacting the homogenate with a silica-based solid surface, thereby extracting the DNA, the RNA, or both the DNA and RNA from the homogenate.

2. The method of claim 1, wherein the solid capture surface is magnetic.

3. The method of claim 1, wherein the at least one anion exchange membrane or the at least one anion exchange bead is functionalized with quaternary ammonium moieties.

4. The method of claim 1, wherein the at least one anion exchange membrane or the at least one anion exchange bead is functionalized with sulfate, sulfonate, tertiary amine, any other IEX group, or any combination thereof.

5. The method of claim 1, wherein the biological sample is plasma, serum, or urine.

6. The method of claim 1, wherein the biological sample is between 0.2 to 20 mL.

7. The method of claim 1, wherein the biological sample is urine.

8. The method of claim 7, wherein the urine is first-catch urine.

9. The method of claim 1, wherein the guanidine thiocyanate-based elution buffer comprises guanidine thiocyanate, a detergent, a buffer substance, or combinations thereof.

10. The method of claim 9, wherein the guanidine thiocyanate-based elution buffer comprises guanidine thiocyanate and at least one of β-mercaptoethanol (BME), tris(2-carboxyethyl)phosphine (TCEP) and dithiothreitol (DTT) a reducing agent.

11. The method of claim 1, wherein step (c) further comprises adding protein precipitation buffer to the homogenate prior to extraction of the DNA, the RNA, or both the DNA and RNA from the homogenate, wherein the protein precipitation buffer has a defined pH range from 3.1 to 4.1.

12. The method of claim 11, wherein the protein precipitation buffer further comprises a transition metal ion.

13. The method of claim 12, wherein the transition metal ion is zinc.

14. The method of claim 1, wherein the concentration of PEG is 0.5-10% (w/v).

* * * * *

UNITED STATES PATENT AND TRADEMARK OFFICE
CERTIFICATE OF CORRECTION

PATENT NO. : 10,808,240 B2
APPLICATION NO. : 16/301176
DATED : October 20, 2020
INVENTOR(S) : Georg Stoll et al.

Page 1 of 1

It is certified that error appears in the above-identified patent and that said Letters Patent is hereby corrected as shown below:

In the Claims

At Column 29, Claim number 10, Line numbers 8-9:
"carboxyethyl)phosphine (TCEP) and dithiothreitol (DTT) a reducing agent."
Should read:
-- carboxyethyl)phosphine (TCEP) and dithiothreitol (DTT). --

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*